US007922740B2

(12) United States Patent
Eidenschink et al.

(10) Patent No.: US 7,922,740 B2
(45) Date of Patent: *Apr. 12, 2011

(54) ROTATABLE CATHETER ASSEMBLY

(75) Inventors: Tracee Eidenschink, Wayzata, MN (US); Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1334 days.

This patent is subject to a terminal disclaimer.

(21) Appl. No.: 10/915,209

(22) Filed: Aug. 10, 2004

(65) Prior Publication Data
US 2005/0187603 A1    Aug. 25, 2005

Related U.S. Application Data

(63) Continuation-in-part of application No. 10/785,449, filed on Feb. 24, 2004, now Pat. No. 7,744,619.

(51) Int. Cl.
*A61M 29/00* (2006.01)
(52) U.S. Cl. ........................................................ 606/194
(58) Field of Classification Search .................. 623/1.11; 606/108, 112, 190–200; 604/108, 165.04, 604/915–920, 103, 103.07, 96.01, 95.03
See application file for complete search history.

(56) References Cited

U.S. PATENT DOCUMENTS

| 4,254,773 A | * | 3/1981 | Waldbillig | 604/534 |
|---|---|---|---|---|
| 4,273,111 A | | 6/1981 | Tsukaya | |
| 4,286,585 A | | 9/1981 | Ogawa | |
| 4,448,195 A | | 5/1984 | Leveen et al. | |
| 4,484,585 A | | 11/1984 | Baier | |
| 4,499,895 A | | 2/1985 | Takayama | |
| 4,503,842 A | | 3/1985 | Takayama | |
| 4,543,090 A | | 9/1985 | McCoy | |
| 4,601,701 A | | 7/1986 | Mueller, Jr. | |
| 4,601,705 A | | 7/1986 | McCoy | |
| 4,753,223 A | | 6/1988 | Bremer | |
| 4,769,005 A | | 9/1988 | Ginsburg et al. | |
| 4,776,337 A | | 10/1988 | Palmaz | |
| 4,790,624 A | | 12/1988 | Van Hoye et al. | |
| 4,793,359 A | | 12/1988 | Sharrow | |
| 4,830,023 A | | 5/1989 | De Toledo et al. | |

(Continued)

FOREIGN PATENT DOCUMENTS

DE        29701758        3/1997

(Continued)

OTHER PUBLICATIONS

U.S. Appl. No. 10/785,449, filed Feb. 24, 2004.

(Continued)

*Primary Examiner* — Anhtuan T Nguyen
*Assistant Examiner* — David Eastwood
(74) *Attorney, Agent, or Firm* — Seager, Tufte & Wickhem, LLC

(57) ABSTRACT

A catheter assembly comprises a catheter shaft, a balloon and a pair of collars engaged to the catheter shaft. Each collar has a body portion and at least one lip portion extending radially outward from the body portion. Each collar has a nonactivated state and an activated state, wherein in the nonactivated state the balloon is rotatable about the collars and each lip portion is constructed and arranged to abut a portion of the balloon to prevent the balloon from moving longitudinally relative thereto. In the activated state the body portion of each collar is sealingly engaged to at least a portion of the balloon.

30 Claims, 10 Drawing Sheets

U.S. PATENT DOCUMENTS

| | | |
|---|---|---|
| 4,838,859 A | 6/1989 | Strassmann |
| 4,846,573 A | 7/1989 | Taylor et al. |
| 4,884,557 A | 12/1989 | Takehana et al. |
| 4,899,731 A | 2/1990 | Takayama et al. |
| 4,906,244 A | 3/1990 | Pinchuk et al. |
| 4,913,141 A | 4/1990 | Hillstead |
| 4,930,494 A | 6/1990 | Takehana et al. |
| 4,950,239 A | 8/1990 | Gahara et al. |
| 4,977,886 A | 12/1990 | Takehana et al. |
| 4,987,314 A | 1/1991 | Gotanda et al. |
| 4,988,356 A | 1/1991 | Crittenden et al. |
| 4,994,071 A | 2/1991 | MacGregor |
| 4,998,923 A | 3/1991 | Samson et al. |
| 5,019,085 A | 5/1991 | Hillstead |
| 5,090,956 A | 2/1992 | McCoy |
| 5,100,933 A | 3/1992 | Tanaka et al. |
| 5,122,154 A | 6/1992 | Rhodes |
| 5,188,111 A | 2/1993 | Yates et al. |
| 5,195,984 A | 3/1993 | Schatz |
| 5,209,728 A | 5/1993 | Kraus et al. |
| 5,219,355 A | 6/1993 | Parodi et al. |
| 5,239,982 A | 8/1993 | Trauthen |
| 5,250,167 A | 10/1993 | Adolf et al. |
| 5,268,082 A | 12/1993 | Oguro et al. |
| 5,290,306 A | 3/1994 | Trotta et al. |
| 5,316,023 A | 5/1994 | Palmaz et al. |
| 5,318,535 A | 6/1994 | Miraki |
| 5,337,732 A | 8/1994 | Grundfest et al. |
| 5,347,987 A | 9/1994 | Feldstein et al. |
| 5,348,537 A | 9/1994 | Wiesner et al. |
| 5,368,015 A | 11/1994 | Wilk |
| 5,389,222 A | 2/1995 | Shahinpoor |
| 5,396,879 A | 3/1995 | Wilk et al. |
| 5,397,305 A | 3/1995 | Kawula et al. .................. 604/96 |
| 5,425,703 A | 6/1995 | Feiring |
| 5,431,645 A | 7/1995 | Smith et al. |
| 5,449,343 A | 9/1995 | Samson et al. |
| 5,449,353 A | 9/1995 | Watanabe et al. |
| 5,477,856 A | 12/1995 | Lundquist |
| 5,482,029 A | 1/1996 | Sekiguchi et al. |
| 5,492,121 A | 2/1996 | Lu |
| 5,492,532 A * | 2/1996 | Ryan et al. ............... 604/103.09 |
| 5,500,181 A | 3/1996 | Wang et al. |
| 5,556,370 A | 9/1996 | Maynard |
| 5,556,700 A | 9/1996 | Kaneto et al. |
| 5,609,627 A | 3/1997 | Goicoecchea et al. |
| 5,624,380 A | 4/1997 | Takayama et al. |
| 5,631,040 A | 5/1997 | Takuchi et al. |
| 5,632,763 A | 5/1997 | Glastra |
| 5,643,278 A | 7/1997 | Wijay |
| 5,645,520 A | 7/1997 | Nakamura et al. |
| 5,649,923 A | 7/1997 | Gregory et al. |
| 5,651,366 A | 7/1997 | Liang et al. |
| 5,662,587 A | 9/1997 | Grundfest et al. |
| 5,683,345 A | 11/1997 | Waksman et al. |
| 5,693,015 A | 12/1997 | Walker et al. |
| 5,697,948 A | 12/1997 | Marin et al. |
| 5,697,971 A | 12/1997 | Fischell et al. |
| 5,720,735 A | 2/1998 | Dorros |
| 5,725,519 A | 3/1998 | Penner et al. |
| 5,749,825 A | 5/1998 | Fischell et al. ..................... 600/3 |
| 5,755,734 A | 5/1998 | Richter et al. |
| 5,755,735 A | 5/1998 | Richter et al. |
| 5,755,778 A | 5/1998 | Kleshinski |
| 5,766,013 A | 6/1998 | Vuyk |
| 5,771,902 A | 6/1998 | Lee et al. |
| 5,772,669 A | 6/1998 | Vrba |
| 5,797,952 A | 8/1998 | Klein |
| 5,824,055 A | 10/1998 | Spiridigliozzi et al. |
| 5,855,565 A | 1/1999 | Bar-Cohen et al. |
| 5,857,962 A | 1/1999 | Bracci et al. |
| 5,873,817 A | 2/1999 | Kokish et al. |
| 5,873,906 A | 2/1999 | Lau et al. |
| 5,876,374 A | 3/1999 | Alba et al. |
| 5,893,868 A | 4/1999 | Hanson et al. |
| 5,906,591 A | 5/1999 | Dario et al. |
| 5,906,640 A | 5/1999 | Penn et al. |
| 5,908,405 A | 6/1999 | Imran et al. |
| 5,916,146 A | 6/1999 | Allotta et al. |
| 5,921,995 A | 7/1999 | Kleshinski |
| 5,935,161 A | 8/1999 | Robinson et al. |
| 5,941,908 A | 8/1999 | Goldsteen et al. |
| 5,951,569 A | 9/1999 | Tuckey et al. |
| 5,957,833 A | 9/1999 | Shan |
| 5,957,929 A | 9/1999 | Brenneman |
| 5,961,546 A | 10/1999 | Robinson et al. |
| 5,961,548 A | 10/1999 | Shmulewitz |
| 6,010,449 A | 1/2000 | Selmon et al. |
| 6,013,092 A | 1/2000 | Dehdashtian et al. |
| 6,017,362 A | 1/2000 | Lau |
| 6,024,752 A * | 2/2000 | Horn et al. ..................... 606/192 |
| 6,027,460 A | 2/2000 | Shturman |
| 6,033,434 A | 3/2000 | Borghi |
| 6,048,361 A | 4/2000 | Von Oepen |
| 6,056,722 A | 5/2000 | Jayaraman |
| 6,056,775 A | 5/2000 | Borghi et al. |
| 6,059,813 A | 5/2000 | Vrba et al. |
| 6,071,234 A | 6/2000 | Takada |
| 6,071,286 A | 6/2000 | Mawad |
| 6,077,297 A | 6/2000 | Robinson et al. |
| 6,090,127 A | 7/2000 | Globerman |
| 6,096,073 A | 8/2000 | Webster et al. |
| 6,099,497 A | 8/2000 | Adams et al. |
| 6,109,852 A | 8/2000 | Shahinpoor et al. |
| 6,110,191 A | 8/2000 | Dehdashtian et al. |
| 6,117,156 A | 9/2000 | Richter et al. |
| 6,117,296 A | 9/2000 | Thomson |
| 6,120,522 A | 9/2000 | Vrba et al. |
| 6,132,450 A | 10/2000 | Hanson et al. |
| 6,143,014 A | 11/2000 | Dehdashtian et al. |
| 6,146,415 A | 11/2000 | Fitz |
| 6,152,944 A | 11/2000 | Holman et al. |
| 6,162,171 A | 12/2000 | Ng et al. |
| 6,165,195 A | 12/2000 | Wilson et al. |
| 6,165,210 A | 12/2000 | Lau et al. |
| 6,187,015 B1 | 2/2001 | Brenneman |
| 6,190,360 B1 | 2/2001 | Iancea et al. |
| 6,190,393 B1 | 2/2001 | Bevier et al. |
| 6,210,380 B1 | 4/2001 | Mauch |
| 6,210,431 B1 | 4/2001 | Power |
| 6,221,090 B1 | 4/2001 | Wilson |
| 6,221,097 B1 | 4/2001 | Wang et al. |
| 6,224,587 B1 | 5/2001 | Gibson |
| 6,238,410 B1 | 5/2001 | Vrba et al. |
| 6,246,914 B1 | 6/2001 | De la Rama |
| 6,249,076 B1 | 6/2001 | Madden et al. |
| 6,254,593 B1 | 7/2001 | Wilson |
| 6,258,052 B1 | 7/2001 | Milo |
| 6,258,073 B1 | 7/2001 | Mauch |
| 6,264,688 B1 | 7/2001 | Herklotz et al. |
| 6,280,466 B1 | 8/2001 | Kugler et al. |
| 6,287,277 B1 | 9/2001 | Yan |
| 6,287,330 B1 | 9/2001 | Johansson et al. |
| 6,290,673 B1 | 9/2001 | Shanley ..................... 604/102.2 |
| 6,299,636 B1 | 10/2001 | Schmitt et al. |
| 6,302,906 B1 | 10/2001 | Goicoechea et al. |
| 6,315,790 B1 | 11/2001 | Gerberding et al. |
| 6,319,275 B1 | 11/2001 | Lashinski et al. |
| 6,322,548 B1 | 11/2001 | Payne et al. |
| 6,352,561 B1 | 3/2002 | Leopold et al. |
| 6,361,544 B1 | 3/2002 | Wilson et al. |
| 6,361,555 B1 | 3/2002 | Wilson |
| 6,364,893 B1 | 4/2002 | Sahatjian et al. |
| 6,371,978 B1 | 4/2002 | Wilson |
| 6,375,660 B1 | 4/2002 | Fischell et al. |
| 6,375,675 B2 | 4/2002 | Dehdashtian et al. |
| 6,379,372 B1 | 4/2002 | Dehdashtian et al. |
| 6,387,120 B2 | 5/2002 | Wilson et al. |
| 6,391,050 B1 | 5/2002 | Broome |
| 6,391,051 B2 | 5/2002 | Sullivan, III et al. |
| 6,406,487 B2 | 6/2002 | Brenneman |
| 6,406,489 B1 | 6/2002 | Richter et al. |
| 6,416,529 B1 | 7/2002 | Holman et al. |
| 6,432,064 B1 | 8/2002 | Hibner et al. |
| 6,436,104 B2 | 8/2002 | Hojebane |
| 6,443,980 B1 | 9/2002 | Wang et al. |
| 6,468,203 B2 | 10/2002 | Belson |

| | | | |
|---|---|---|---|
| 6,471,672 B1 | 10/2002 | Brown et al. | |
| 6,475,166 B1 | 11/2002 | Escano | |
| 6,475,639 B2 | 11/2002 | Shahinpoor et al. | |
| 6,482,211 B1 | 11/2002 | Choi | |
| 6,488,694 B1 | 12/2002 | Lau et al. | |
| 6,508,835 B1 | 1/2003 | Shaolian et al. | |
| 6,514,237 B1 | 2/2003 | Maseda | |
| 6,514,281 B1 | 2/2003 | Blaeser et al. | |
| 6,520,983 B1 | 2/2003 | Colgan et al. | |
| 6,520,988 B1 | 2/2003 | Colombo et al. | |
| 6,530,947 B1 | 3/2003 | Euteneuer et al. | |
| 6,533,805 B1 | 3/2003 | Jervis | |
| 6,540,719 B2 | 4/2003 | Bigus et al. | |
| 6,545,097 B2 | 4/2003 | Pinchuk et al. | |
| 6,554,841 B1 | 4/2003 | Yang | |
| 6,582,459 B1 | 6/2003 | Lau et al. | |
| 6,583,533 B2 | 6/2003 | Pelrine et al. | |
| 6,586,859 B2 | 7/2003 | Kornbluh et al. | |
| 6,589,251 B2 | 7/2003 | Yee et al. | |
| 6,589,262 B1 | 7/2003 | Honebrink et al. | |
| 6,592,616 B1 * | 7/2003 | Stack et al. | 623/1.17 |
| 6,596,020 B2 | 7/2003 | Vardi et al. | |
| 6,599,315 B2 | 7/2003 | Wilson | 623/1.11 |
| 6,602,226 B1 | 8/2003 | Smith et al. | |
| 6,607,506 B2 | 8/2003 | Kletschka | |
| 6,613,067 B1 | 9/2003 | Johnson | |
| 6,629,981 B2 | 10/2003 | Bui et al. | |
| 6,664,718 B2 | 12/2003 | Pedrine et al. | |
| 6,669,718 B2 | 12/2003 | Besselink | |
| 6,679,836 B2 | 1/2004 | Couvillon, Jr. | |
| 6,733,520 B2 | 5/2004 | Yang et al. | |
| 6,749,556 B2 | 6/2004 | Banik | |
| 6,752,433 B2 | 6/2004 | Frost | |
| 6,764,504 B2 | 7/2004 | Wang et al. | |
| 6,770,027 B2 | 8/2004 | Banik et al. | |
| 6,783,542 B2 | 8/2004 | Eidenschink | |
| 6,802,856 B2 | 10/2004 | Wilson | |
| 6,835,173 B2 | 12/2004 | Couvillon, Jr. | |
| 6,849,085 B2 | 2/2005 | Marton | |
| 6,884,258 B2 | 4/2005 | Vardi et al. | |
| 6,969,395 B2 | 11/2005 | Eskuri | |
| 7,018,402 B2 | 3/2006 | Vito et al. | |
| 7,063,671 B2 | 6/2006 | Couvillon, Jr. | |
| 7,070,613 B2 | 7/2006 | Weber et al. | |
| 7,225,518 B2 | 6/2007 | Eidenschink et al. | |
| 7,314,480 B2 | 1/2008 | Eidenschink et al. | |
| 7,331,969 B1 | 2/2008 | Inganas et al. | |
| 7,338,509 B2 | 3/2008 | Mattison | |
| 7,367,989 B2 | 5/2008 | Eidenschink | |
| 7,379,852 B2 | 5/2008 | Freitas et al. | |
| 7,396,582 B2 | 7/2008 | Claude et al. | |
| 7,399,311 B2 | 7/2008 | Bertolino et al. | |
| 2002/0019664 A1 | 2/2002 | Douglas | |
| 2002/0038140 A1 | 3/2002 | Yang et al. | |
| 2003/0033001 A1 | 2/2003 | Igaki | |
| 2003/0055483 A1 | 3/2003 | Gumm | |
| 2003/0055484 A1 | 3/2003 | Lau et al. | |
| 2003/0195546 A1 | 10/2003 | Solar et al. | |
| 2003/0236531 A1 * | 12/2003 | Couvillon, Jr. | 606/113 |
| 2004/0068161 A1 | 4/2004 | Couvillon, Jr. | |
| 2005/0149161 A1 | 7/2005 | Eidenschink et al. | |
| 2005/0149176 A1 | 7/2005 | Heggestuen et al. | |
| 2005/0154442 A1 | 7/2005 | Eidenschink et al. | |
| 2005/0165439 A1 | 7/2005 | Weber et al. | |
| 2005/0182473 A1 | 8/2005 | Eidenschink et al. | |
| 2005/0187603 A1 | 8/2005 | Eidenschink et al. | 623/1.11 |
| 2005/0273149 A1 | 12/2005 | Tran et al. | |
| 2006/0206188 A1 | 9/2006 | Weber et al. | |
| 2007/0088256 A1 | 4/2007 | Intoccia | |

FOREIGN PATENT DOCUMENTS

| | | |
|---|---|---|
| ES | 2048086 | 3/1994 |
| ES | 2062930 | 12/1994 |
| FR | 2678508 | 1/1993 |
| GB | 2227020 | 7/1990 |
| JP | 8066351 | 3/1996 |
| JP | 8322783 | 12/1996 |
| JP | 10014863 | 1/1998 |
| WO | WO 01/58973 | 8/2001 |
| WO | WO 03/017872 | 3/2003 |
| WO | WO 03/055414 | 7/2003 |
| WO | WO 03/094800 | 11/2003 |
| WO | WO 2004/000141 | 12/2003 |
| WO | WO 2005/025458 | 3/2005 |

OTHER PUBLICATIONS

Bar-Cohen, "Application of Dielectric Elastomer EAP Actuators," Electroactive Polymer (EAP) Actuators as Artificial Muscles, Chapter 16, pp. 457-495, 2001.

Bar-Cohen, "EAP History, Current Status, and Infrastructure," Electroactive Polymer Actuators (EAP) as Artificial Muscles, Chapter 1, pp. 3-43, 2001.

Bar-Cohen, "EAP Applications, Potential, and Challenges," Electroactive Polymer (EAP) Actuators as Artificial Muscles, Chapter 21, pp. 615-659, 2001.

Bar-Cohen et al., "Electro-Active Polymer (EAP) Actuators for Planetary Applications," Proceedings of SPIE Annual International Symposium on Smart Structures and Materials, 5 pages, 1999.

Bar-Cohen, "Electroactive Polymers as Artificial Muscles-Capabilities, Potentials and Challenges," Handbook on Biommetics, Section 11, Chapter 8, Aug. 2000.

Bar-Cohen, "Transition of EAP Material from Novelty to Practical Applications—Are we there Yet?," Proceedings of SPIE vol. 4329, pp. 1-6, Mar. 5-8, 2001.

Bar-Cohen, "WorldWide ElectroActive Polymers WW EAP (Artificial Muscles) Newsletter," vol. 3, No. 1, pp. 1-14, Jun. 2001.

Brock, "Review of Artificial Muscle Based on Contractile Polymers," 12 pages, May 9, 2002.

Buckley, "EAP DARPA," Defense Sciences Office, 8 pages, Jan. 2002.

Cho et al., "Development of Micro Inchworm Robot Actuated by Electrostrictive Polymer Actuator," Proceedings of SPIE , vol. 4329, pp. 466-474, Mar. 5-8, 2001.

Foley et al., "Bifurcation Lesion Stenting," The Thoraxcentre Journal, vol. 8/4, 5 pages, 1998.

Goodell, "Laser Thrombolysis (LT) for Stroke," http://www.providence.org/Oregon/Programs_and_Services/Research/Laser_Center/Lt_Stroke..., 3 pages, Updated Mar. 26, 2001, printed Oct. 2, 2002.

Gulch et al., "Characterization of Electroactive Behavior and of Progress in Developments and Applications of Ionic Polymer Gels," Proceedings of SPIE vol. 4695, pp. 367-377, 2002.

http://ais.gmd.de/BAR/snake.html, "GMD-SNAKE, Robot-Snake with Flexible Real-Time Control," 3 pages, last updated Jan. 10, 2001, printed Dec. 27, 2001.

http://nanobio.snu.ac.kr/eng/research_5.html, "Electroactive Polymer," Nano Bioelectronics & Systems Research Center, 1 page, printed Feb. 5, 2004.

http://omlc.ogi.edu/projects/lt/, "Laser Thrombolysis," 9 pages, Dec. 12, 1996.

http://piaggio.ccii.unipi.it/cathe.htm, "Smart Catheters," 1 page, printed Aug. 27, 2001.

http://polysep.ucla.edu/Research20%Advances, "Polymers Separations Research Lab (PolySep)," 12 pages, printed Feb. 5, 2004.

http://robby.caltech.edu/~chen/res-medical.html, "Snake-Like Robot Endoscopes," 2 pages, updated Aug. 14, 1996, printed Dec. 27, 2001.

http://virtualskies.arc.nasa.gov/reasearch/youDecide, "Electroactive Polymers 2: Ionic and Conductive Polymers," 2 pages, printed Feb. 5, 2004.

http://www.agip.sicences.univ-metz.fr/mihalach/Coperinicus_projet_engl.html, "Snake-Like Flexible Micro-Robot," 6 pages, printed Dec. 27, 2001.

http://www.azom.com/detailsasp?ArticleID=885, Electroactive Polymers—EAPs, 7 pages, Feb. 5, 2004.

http://www.designinsite.dk/htmsider/m1328.htminsider, 3 pages, printed Mar. 11, 2004.

http://www.erg.sri.com/automation/actuators.html, "Artificial Muscle Transducers," 3 pages, printed Feb. 5, 2004.

http://www.nasatech.com/Briefs/Oct01/NPO20613.html, "Miniature Electroactive-Polymer Rakes," 2 pages, Feb. 5, 2004.

Ikuta et al., "Shape Memory Alloy Servo Actuator System with Electric Resistance Feedback and Application for Active Endoscope," IEEE Internation Conference on Robotics and Automation, pp. 427-430, Apr. 24-29, 1988.
Immerstrand et al., "Conjugated-Polymer Micro-and Milliactuators for Biological Applications," MRS Bulletin, pp. 461-464, Jun. 2002.
Jager et al., "Applications of Polypyrrole Microactuators," SPIE, vol. 3669, pp. 377-384, Mar. 1999.
Jager et al., "Microfabricating Conjugated Polymer Actuators," Science, vol. 290, pp. 1540-1545, Nov. 24, 2000.
Kubler et al., "An Endoscopic Navigation System," Medicine Meets Virtual Reality, pp. 253, 255, 2001.
Kubler et al., "Endoscopic Robots," Proceedings of the 3$^{rd}$ International Conference on Medical Image Computing and Computer-Assisted Intervention—MICCAI, pp. 949-955, 2000.
Madden et al., "Conducting Polymer Actuators as Engineering Materials," Proceedings of SPIE vol. 4695, 2002.
Madden et al., "Polypyrrole Actuators: Modeling and Performance," Proceedings of SPIE vol. 4329, pp. 72-83, Mar. 5-8, 2001.
Madden, "Conducting Polymer Actuators," Abstract, 2 pages, Sep. 2000.
Mazzoldi et al., "Conductive Polymer Based Structures for a Steerable Catheter," Proceedings of SPIE vol. 3987, pp. 273-280, 2000.
Nakamura et al., "Techniques for Palmaz-Schatz Stent Deployment in Lesions with a Large Side Branch," Catheterization and Cardiovascular Diagnosis, vol. 34, pp. 353-361, 1995.
Nam, "Electroactive Polymer (EAP) Actuators and Devices for Micro-Robot Systems," 1 page, Nov. 28, 2000.
Oda et al., "Fork Stenting for Bifurcation Lesion," Journal of Interventional Cardiology, vol. 9, No. 6, pp. 445-454, Dec. 1996.
Otero et al., "EAP as Multifunctional and Biommetic Materials," SPIE, vol. 3669, pp. 26-34, Mar. 1999.
Palmaz et al., "Aortic Bifurcation Stenosis: Treatment with Intravascular Stents," Journal of Vascular and Interventional Radiology, vol. 2, No. 3, pp. 319-323, Aug. 1991.
Peirs et al., "Miniature Parallel Manipulators for Integration in a Self-Propelling Endoscope," 1 page, IMechs Workshop, Oct. 27, 1999.
Pelrine et al., "Applications of Dielectric Elastomer Actuators," Proceedings of SPIE vol. 4329, 16 pages, Mar. 5-8, 2001.
Pomerantz et al., "Distortion of Palmaz-Schatz Stent Geometry Following Side-Branch Balloon Dilation Through the Stent in a Rabbit Model," Catheterization and Cardiovascular Diagnosis, vol. 40, pp. 422-426, Oct. 30, 1997.
Rocchia et al., "Exploiting Conducting Polymer Fiber Radial Expansion for Bioinspired Actuation," Proceedings of SPIE vol. 5051, pp. 453-457, 2003.
Sahoo et al., "Actuators Based on Electroactive Polymers," Current Science, vol. 81, No. 7, pp. 743-746, Oct. 10, 2001.
Sansinena et al., "Chapter 7, Conductive Polymers," Electroactive Polymer Actuators (EAP) as Artificial Muscles, pp. 193-221, 2001.
Santa et al., "Intravascular Microcatheters Steered by Conducting Polymer Actuators," 18$^{th}$ International Conference of the IEEE Engineering in Medicine and Biology Society, pp. 2203-2204, 1996.
Schampaert et al., "The V-Stent: A Novel Technique for Coronary Bifurcation Stenting," Catheterization and Cardiovascular Diagnosis, vol. 39, No. 3, pp. 320-326, Nov. 1996.
Smela et al., "Thiol-Modified Pyrrole Monomers: 1. Synthesis, Characterization, and Polymerization of 1-(2-Thioethyl) Pyrrole and 3-(2-Thioethyl) Pyrrole," Langmuir, vol. 14, 2970-2975, May 26, 1998.
Smela, "Conjugated Polymer Actuators for Biomedical Applications," Advanced Materials, vol. 15, No. 6, pp. 481-494, Mar. 17, 2003.
Smela, "Microfabrication of PPy Microactuators and Other Conjugated Polymer Devices," Journal of Micromechanics and Microengineering, vol. 9, pp. 1-18, 1999.
Smela et al., "Electrochemically Driven Polypyrrole Bilayers for Moving and Positioning Bulk Micromachined Silicon Plates," Journal of Microelectromechanical Systems, vol. 8, No. 4, pp. 373-383, Dec. 1999.
Wax et al., "Compliant Actuators Based on Electroactive Polymers," Materials Research Society Proceedings, vol. 600, pp. 3-11, 2000.
Zhou et al., "Actuators for the Cochlear Implant," Synthetic Metals, vol. 135-136, pp. 39-40, 2003.

* cited by examiner

ROTATABLE CATHETER ASSEMBLY

CROSS-REFERENCE TO RELATED APPLICATIONS

This application is a Continuation-in-part application of U.S. Pat. No. 7,744,619, entitled Rotatable Catheter Assembly, and which was filed Feb. 24, 2004, the entire contents of which is incorporated herein by reference.

STATEMENT REGARDING FEDERALLY SPONSORED RESEARCH

Not Applicable

BACKGROUND OF THE INVENTION

Description of the Related Art

Stent delivery systems for deployment of one or more stent bodies at or around a vessel bifurcation have been proposed. Often such stents generally have an opening which allows for unimpeded blood flow into one or more side branch arteries, and/or through which an additional stent body may be deployed. However, problems are still encountered in orienting a stent relative to the side branch at the bifurcation of the primary and secondary passages. Moreover, such bifurcated assemblies are typically specially manufactured at an increased cost over a more standard stent intended for single vessel deployment.

In delivering a stent to a vessel location, many current devices rely on either passive torque (e.g., pushing the stent forward and allowing the stent that is fixed on the guidewire/balloon to passively rotate itself into place) or creating torque from outside of the patient to properly orient the medical device in the passage. Such catheter assemblies include those described in U.S. Pat. No. 5,749,825; U.S. Pat. No. 6,599,315 and U.S. Pat. No. 6,290,673 the entire content of each of which being incorporated herein by reference.

Unfortunately such devices still often require a significant portion of the catheter assembly in addition to the balloon to be subjected to torque in order to align the stent with the side branch opening of the bifurcation. Subjecting the catheter as well as a vessel to such extraneous torque may be considered undesirable.

Thus, a need exists to provide a catheter which is capable of allowing a medical device such as a stent to be easily maneuvered and aligned at a vessel bifurcation or other location without the need to torque or rotate the entire catheter shaft in order to align the stent at a vessel bifurcation. Various devices and methods described herein address this need by providing a catheter system with a rotatable balloon about which a stent may be mounted on or engaged to. The rotatable balloon is independently rotatable relative to the inner and/or outer catheter shafts thereby eliminating the need to apply torque to the catheter shaft to align the stent at a vessel bifurcation.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the present invention is directed to catheter systems wherein the catheter comprises a balloon which is independently rotatable about the catheter shaft or shafts. In some embodiments, a catheter system employs electro-active polymer (EAP) materials in the form of a collar or balloon waist to provide the balloon with the ability to be selectively rotated about the catheter shaft or shaft. Systems employing such EAP collars are featured in U.S. patent application Ser. No. 10/785,449, entitled Rotatable Catheter Assembly, and filed Feb. 24, 2004, of which the entire contents are incorporated herein by reference.

As described in the aforementioned U.S. application collars are at least partially constructed of an electro-active polymer (EAP) which expands to a predetermined extent upon exposure to an electric current. In some embodiments the collars are exposed to the electric current by a conductive element. A second conductive element may be provided by exposing the fluid that inflates the balloon, which is typically saline and/or a radiopaque solution) to a similar electrical current via a conductive element within the balloon. In some embodiments the EAP material of the collar and/or the collar itself will expand about 0.5% to about 20% expansion in a predetermined manner and/or direction when subjected to an electric current of 0.001 microAmps to 1 milliAmps (−2 to +2 V). In at least one embodiment a collar is constructed of one or more conductive elements such as gold, silver, platinum, etc., which is at least partially surrounded by a layer of EAP material.

In embodiments where the collars are fixed to the catheter shaft, prior to exposure to the electric current the collars define an outside diameter which is sufficiently less than the inner diameter of the balloon waists which are respectively disposed there about so as to allow the waists, and thus the balloon body extending there between, to freely rotate about the collars. When the collars are exposed to the electric current through one or more conductive members within and/or adjacent to the catheter shaft the collars will expand and thus effectively push against the respective balloon waists, effectively sealing the interior of the balloon which may then be expanded.

In order to get an electric current to a collar, in some embodiments a conductive wire or member of gold, gold plated SS, Nitinol, silver coated SS, Elgiloy, etc. extends from a current source to a collar through or adjacent to the catheter shaft. In some embodiments the conductive member is in the form of an insulated wire or other member which engages the collar via an exposed end which extends through an opening in the catheter shaft. Such a member may be co-extruded with one or more catheter shafts and/or balloon. A proximal end of the wire is engaged to a current source which may be activated to transmit the current through the wire to the collar when desired. In at least one embodiment a conductive member is at least partially contained within one or more lumens defined by the catheter.

In some embodiments a collar is bonded, welded, adhesively engaged, mechanically engaged or otherwise engaged to a portion of the catheters shaft underlying a waist of the balloon which is rotatable thereabout. In some embodiments, where the collar is fixed to a balloon waist, the waist may be reinforced with one or more layers of transition material positioned between the collar and the balloon waist in order to facilitate engagement there between. In some embodiments the waist may likewise be reinforced. In some embodiments a transition material includes but is not limited to: Plexar, Selar, EMS Hytrel, and other similar materials. In at least one embodiment the collar is integral with the catheter shaft. In at least one embodiment a collar comprises only EAP material.

In some embodiments the catheter comprises one or more support members or rings which support the region of the catheter shaft(s) about which the collars are mounted. A support ring may be constructed of one or more materials including but not limited to: Polyamide, Nylon, Pebax, Acetyl, PTFE, HDPE, PI, PET, Christamid, Vestimid, metal reinforced polymers, braided reinforced polymers, Stainless steel, Nitinol, etc.

In some embodiments the catheter is disposed about a primary guidewire. In at least one embodiment the catheter is a fixed wire catheter. In some embodiments a secondary guidewire housing through which a side branch or secondary guidewire is positioned. In some embodiments the secondary guidewire housing is engaged to the balloon. In at least one embodiment the secondary guidewire housing is positioned at least partially under the stent prior to delivery.

In some embodiments the secondary guidewire extends into a side branch of a bifurcation through a secondary opening of the stent. By advancing the catheter along the secondary guidewire as the catheter is advanced through the main vessel to the bifurcation rotation will be imparted to the balloon to orient the secondary opening of the stent and/or the secondary guidewire housing with the side branch of the vessel bifrcation. When properly oriented the collars are subjected to an electric current thereby imparting the balloon with a fluid seal sufficient to allow inflation of the balloon.

These and other embodiments which characterize the invention are pointed out with particularity in the claims annexed hereto and forming a part hereof However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
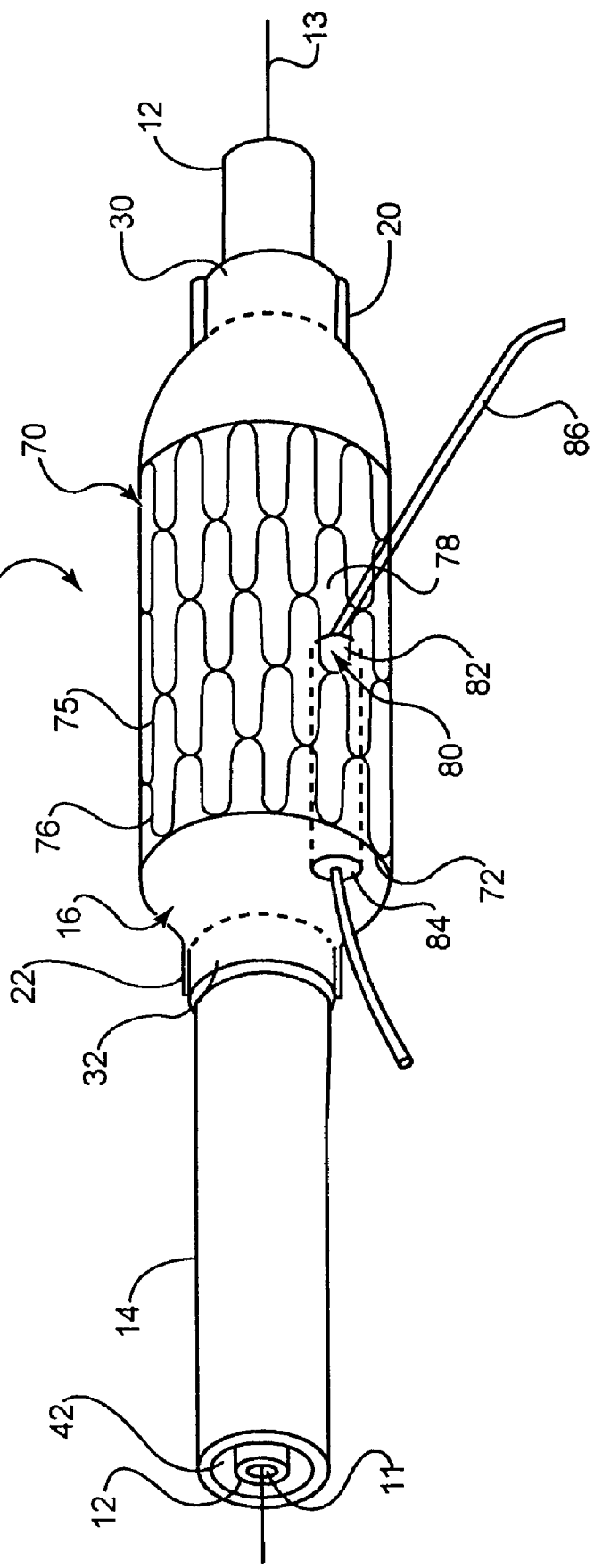
FIG. 1 is a perspective view of an embodiment of the invention comprising a catheter assembly having a rotatable balloon.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring now to the drawings which are for the purposes of illustrating embodiments of the invention only and not for purposes of limiting same, in at least one embodiment of the invention, an example of which is shown in FIG. 1, a catheter assembly 10 comprises an inner catheter shaft 12, an outer catheter shaft 14 and a rotatable balloon 16 rotatably engaged to one or both shafts 12 and 14.

Balloon 16 may be a typical angioplasty, stent delivery balloon or other inflatable member which may be used or incorporated into a catheter assembly. Typically the wall thickness of the waists 20 and 22 of the balloon 16 will be thicker than the thickness of the balloon body which extends there between. In some cases the thickness of one or both waists is about twice that of the balloon body but may be about 10 times more resistant to radial pressures.

In order to allow the balloon 16 to rotate freely relative to the shaft or shafts 12 and 14, each waist 20 and 22 of the balloon 16 is disposed about a collar 30 and 32 respectively. Collars 30 and 32 are at least partially constructed of EAP material such including of Poly-pyrrole (PPY), Poly-Aniline (PAni), Poly-Thiofene (PTH), Poly-Paraphenylene Vinylene (PPV), Nafion, or any other ionic electro-active polymer that is considered to have low voltage, low speed, high stress (up to 500 MPa), characteristics. EAP materials have the unique characteristic of expanding in size when exposed to an electric current of predetermined current or voltage. For example, in some embodiments the EAP material of the collar and/or the collar itself will expand about 0.5% to about 20% when exposed to an electric current of 0.001 microAmps to 1 milliAmps (−2 to +2 V).

Another material which the collars 30 and 32 can be at least partially constructed from is commonly referred to as "bucky paper". Bucky paper is a carbon nano-tube structure which like EAP material is capable of expanding in size when exposed to a predetermined electric current or voltage. Bucky paper however is capable of an expansion of up to about 300%.

EAP materials and some of their notable characteristics are described in an article entitled *Electro-Active Polymer Actuators for Planetary Applications* by Y. Bar-Cohen et al. and published in Paper No. 3669-05 of the Proceedings of SPIE Annual International Symposium on Smart Structures and Materials, March 1999, Newport Beach, Calif. SPIE Copyright 1999, the entire contents of which being incorporated herein by reference.

Bucky paper and its characteristics are described in an article entitled *Pneumatic Actuator Response from Carbon Nanotube Sheets* by Geoffrey M. Spinks et al. and published in Vol. 706 of the Material Research Society Symposium Procedure of the Material Research Society 2002 (Z9.22.1-Z9.22.6), the entire contents of which being incorporated herein by reference.

As a result of EAP materials, as well as materials such as bucky paper, herein after collectively referred to as electro-active materials, unique expansion characteristics a collar comprising electro-active materials, such as collars 30 and 32, may be formed to have a non-activated shape and an activated shape that is different or larger than the non-activated shape.

Non-activated refers to the condition of the collars 30 and 32 before the collars are exposed to an electric current sufficient to activate the EAP material. Activated refers to the condition of the collars 30 and 32 when the collars are being exposed to an electric current sufficient to activate the expansion of the EAP material.

Figure 2:
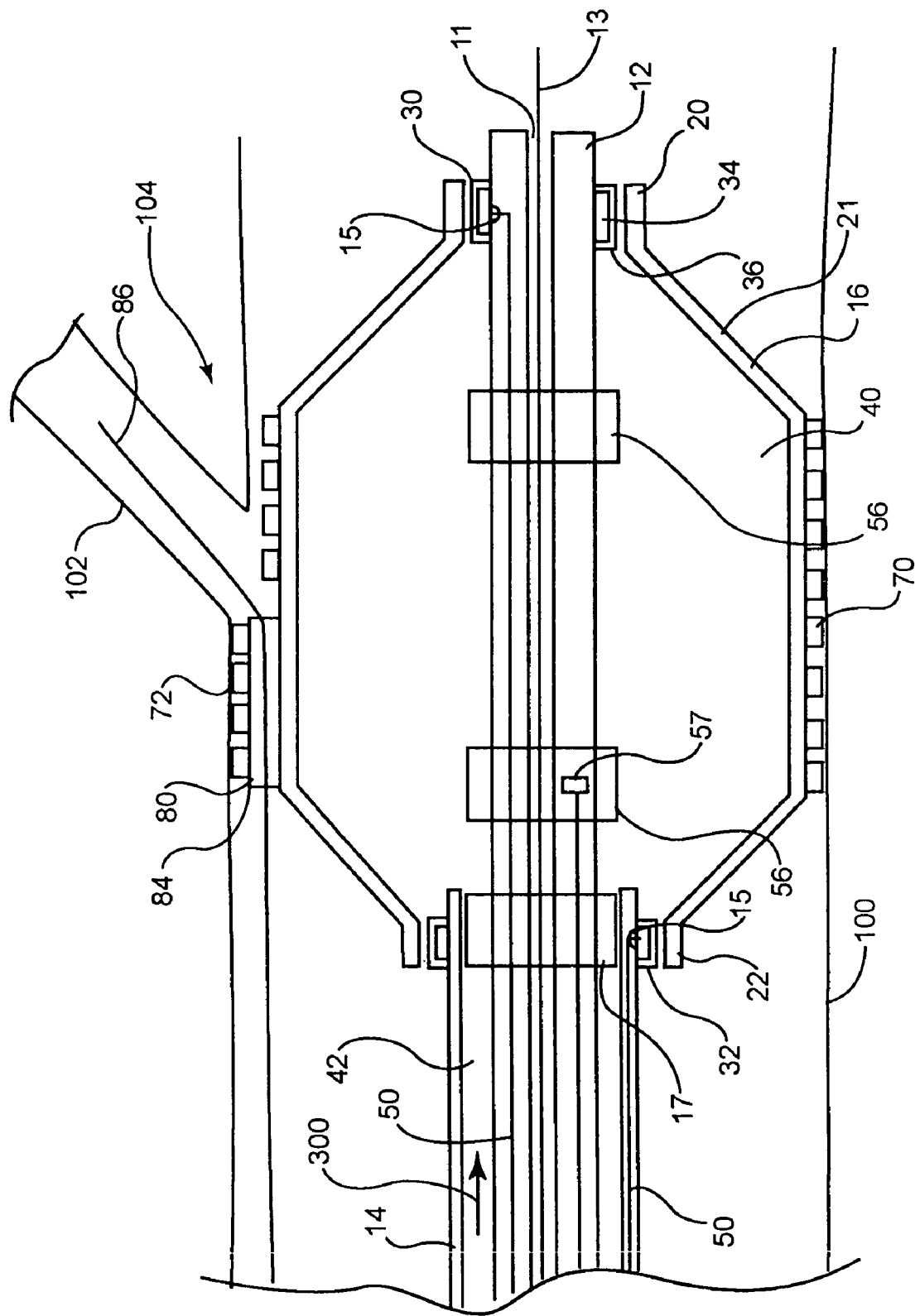
FIG. 2 is a longitudinal cross-sectional view of the embodiment shown in FIG. 1 being advanced to a vessel bifurcation and prior to balloon expansion.

In the embodiment shown in FIG. 2. the collars 30 and 32 are depicted in the non-activated state. In this state, collar 30 is fixedly engaged or integral with the inner shaft 12, and collar 14 is fixedly engaged or integral with the outer shaft 14 of the assembly 10.

The collars 30 and 32 are fixedly engaged about shafts 12 and 14 respectively. In the non-activated state, the balloon 16 is rotatably disposed about the collars 30 and 32 such that the distal waist 20 of the balloon 16 is rotatably disposed about the distal collar 30 and the proximal waist 22 of the balloon 16 is rotatably disposed about the proximal collar 32 of the balloon 16. In the non-activated state each collar 30 and 32 has an outer diameter, or is sized and shaped, so that the balloon waists 20 and 22 are freely rotatable about the respective collars 30 and 32. In the activated state the collars 30 and 32 expand outward to engaged the waists 20 and 22 such as in the manner shown in FIG. 3. By engaging the waists 20 and 22 in this manner the interior 40 of the balloon 16 is made effectively fluid tight against the collars 30 and 32 thereby allowing the balloon to be expanded such as by inflation via an inflation fluid through inflation lumen 42.

Figure 3:
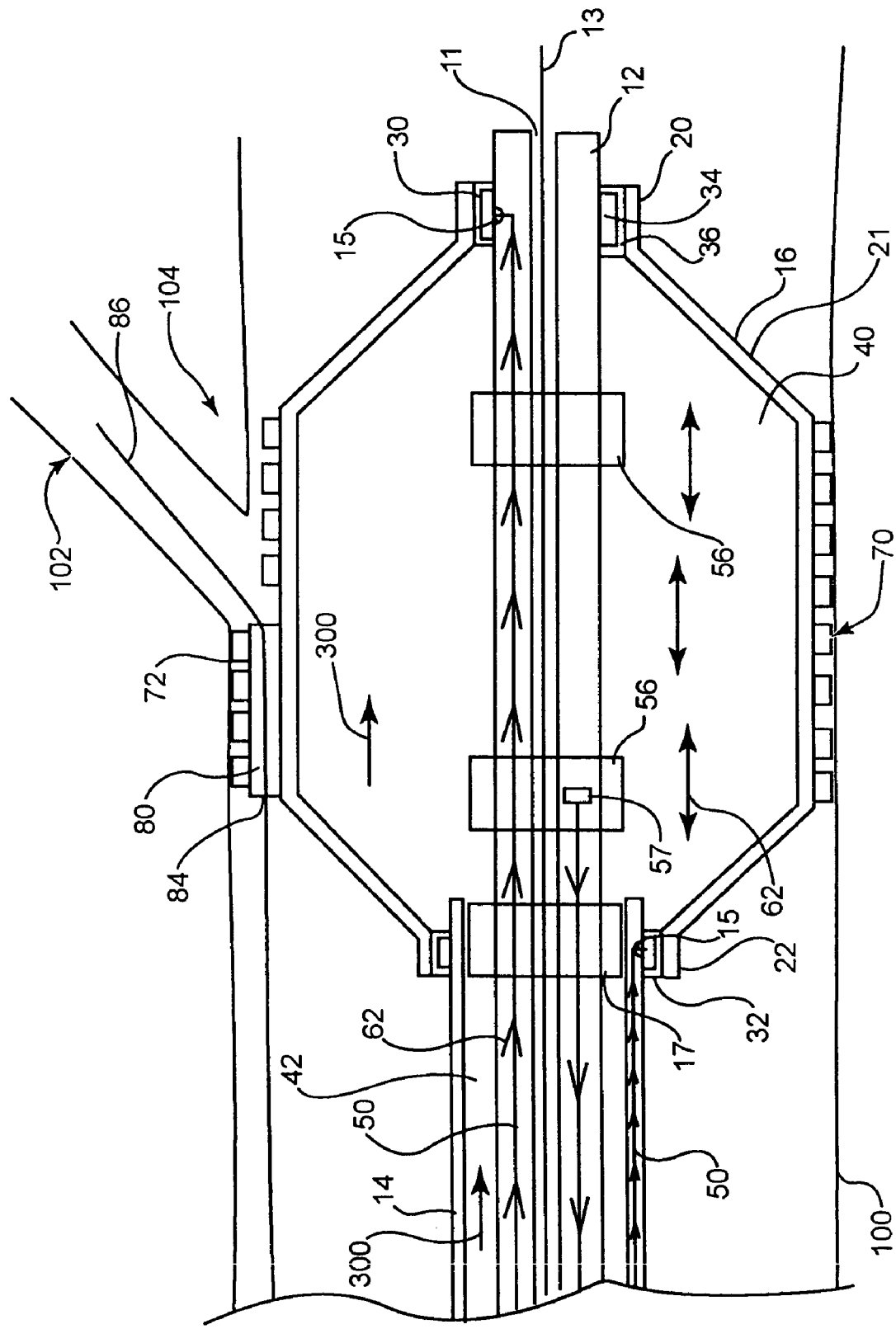
FIG. 3 is a longitudinal cross-sectional view of the embodiment shown in FIG. 2 shown during expansion of the balloon.

In some embodiments, such as in the example shown in FIGS. 2-3, it may be beneficial to support the distal end of the outer shaft 14 with a support ring or member 17. The support ring may be disposed about the inner shaft 12 and/or may be merely internally engaged to the outer shaft 14. In some embodiments the ring 17 is an extension of the outer shaft 14. In some embodiments the ring 17 extends between the inner shaft 12 and the outer shaft 14 but defines one or more openings there through which further define the inflation lumen 42. Ring 17 may be constructed of one or more materials including but not limited to: stainless steel coil, stainless steel stent like structure, stainless steel spiral cut hypotube, Nitinol, acetyl, PI, HDPE, LX2/TR55, Nanocomposites, Ceramics. In some embodiments the length of the ring 17 will be approximately the same length as the collar 32 and/or 30 which it supports.

In some embodiments the inner shaft 12 has one or more bands 56 of radiopaque material. In some embodiments a band(s) 56 is detectable by imaging modalities such as X-Ray, MRI or ultrasound.

Figure 4:
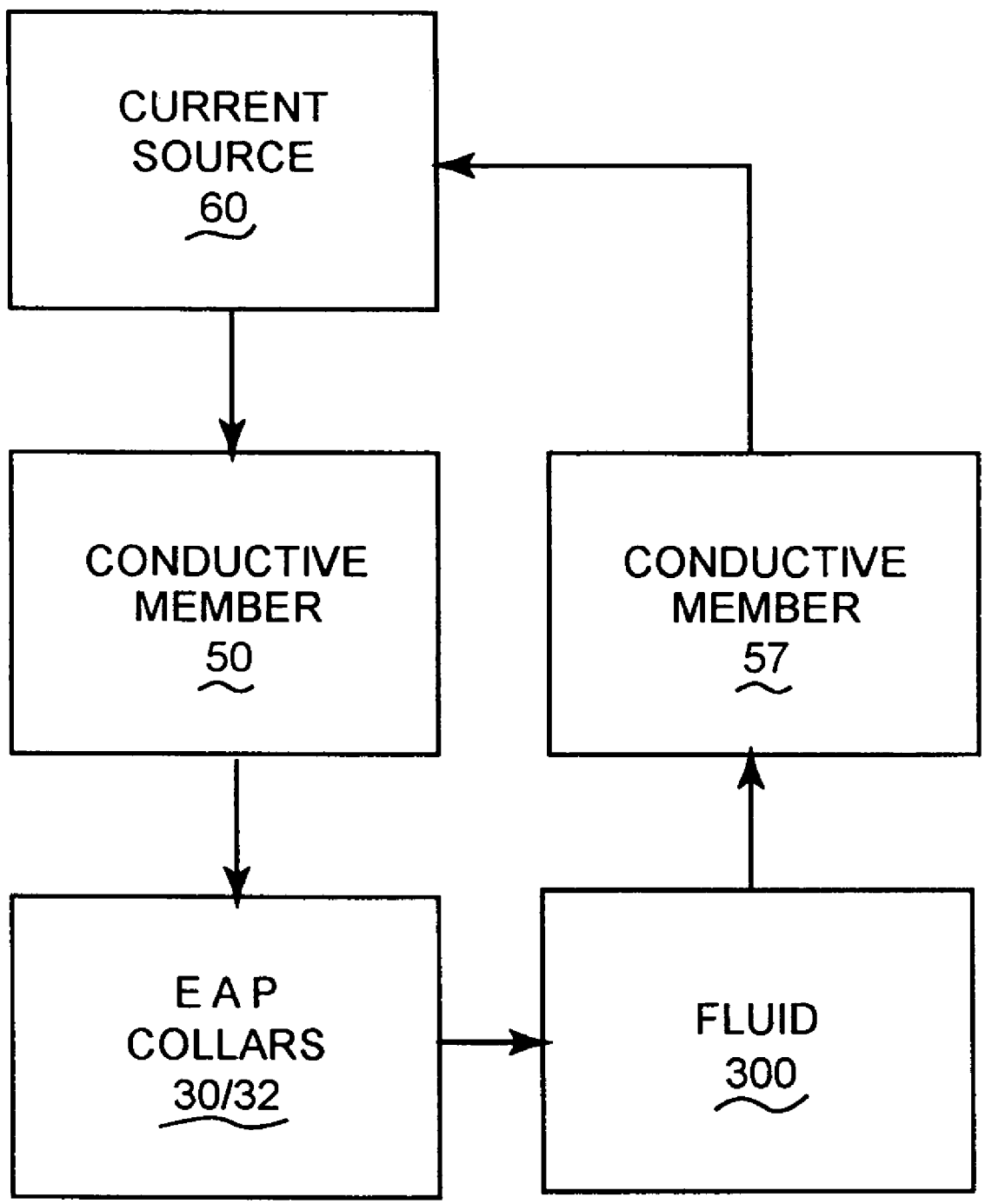
FIG. 4 is a block diagram illustrating the conductive relationship of the catheter assembly shown in FIG. 1 with a source of electric current.

As shown in FIGS. 2-3, one or more conductive wires or other members 50 may extend from a proximal region of the catheter 10 to the collars 30 and 32. A current source 60, as depicted in the circuit diagram of FIG. 4, is in communication with the wire(s) 50, which when activated, transmits the electric current, illustrated by arrows 62 in FIG. 2-3, to the wires 50 and collars 30 and 32, thereby causing expansion of the EAP material in the collars to sealingly engage the collars 30 and 32 to the waists 20 and 22, respectively, of the balloon 16. The current 62 traverses a circuit through the members 50 and collars 30 and 32. The electric circuit may be completed as a result of the presence of saline or other fluid 300 of an electrically conductive nature which is used to expand the balloon 16. The fluid 300 is in electric communication with a conductive member or conductor 57 positioned within the balloon interior. In some embodiments the conductor 57 is in electric communication with one or more marker bands 56. In some cases the conductive nature of some bodily fluids may also be utilized to complete the circuit.

Wires 50 maybe co-extruded with and/or within the material of either or both catheter shafts 12 and 14. An opening 15 in the shaft(s) exposes the wire 50 to the collars 30 and 32 in the manner shown in FIGS. 2-3. Alternatively, the catheter assembly 10 may define any number of lumens through which a wire or wires may be positioned. In some embodiments a wire 50 may extend at least partially through the inflation lumen 42 to one or both collars 30 and 32.

As indicated above the collars 30 and 32 are at least partially constructed of one or more EAP materials. However, in order to more effectively transmit the electric current to the EAP material in some embodiments, such as shown in FIGS. 2-3, the collars 30 and 32 include a conductive member or marker 34 about which at least one layer 36 of EAP material is engaged. The markers 34 may be any type of conductive material or materials and is preferably biocompatible. Appropriate materials for the construction of the markers 34 include but are not limited to, gold, platinum, nitinol, silver, etc. The layer 36 of EAP material may partially or entirely surround the marker 34. The marker 34 may be configured to have a shape similar to that of the layer 36 but on a reduced scale or may have a different shape, size or configuration than that of the layer 36. For example, in some embodiments the marker 34 may comprise a plurality of conductive strips over or about which the layer 36 is disposed.

In at least one embodiment collars 30 and 32 are constructed of a conductive member 34 of gold and at least one layer 36 of PPy which is deposited thereon by electro polymerization. A description of this process is described n an article entitled Microfabricating Conjugated Polymer Actuators by Edwin W. H. Jager et al. which was published in Vol. 290 of the journal Science on Nov. 24, 2000, the entire contents of which are incorporated herein by reference.

In the embodiment depicted in FIGS. 2-3, the collars 30 and 32 are constructed so that at least a portion of the inside surface of the collar is defined by a marker 34. This allows direct contact of the conductive material of the marker to be directly engaged to the conductive wire 50. In this manner the current received by the marker may be distributed to the surrounding layer of EAP material in a substantially uniform manner to allow the EAP material engaged thereto to expand in a substantially uniform manner.

In the various embodiments shown in FIGS. 2-3, prior to electric activation of the collars 30 and 32, the balloon 16 is freely rotatable about the catheter shafts 12 and 14. This capacity to freely rotate allows a stent 70 mounted on the balloon 16 to be rotationally oriented within a body vessel 100 during advancement of the assembly 10 without necessitating torquing of the catheter shafts 12 and/or 14. Because the balloon 16 is freely rotatable, it is desirable to provide the balloon 16 with a mechanism which allows the balloon 16 to be rotated to a desired position.

In the various embodiments described herein the catheter assembly 10 may be a fixed wire catheter or any other catheter design. In the embodiment depicted in FIGS. 1-3 for example the catheter is an over the wire design wherein the inner shaft 12 defines a primary guidewire lumen 11 along which a primary guidewire 13 may be advanced.

In some embodiments, such as are illustrated in FIGS. 1-3, such a mechanism is comprised of a secondary guidewire housing 80. Housing 80 may be comprised of an tubular member which defines a secondary guidewire lumen 84 through which a secondary guidewire 86 may be advanced. The housing 80 is engaged to the balloon 16 or defined by the balloon wall as desired. The housing 80 may be comprised of one or more tubular members 82. Where multiple members 82 are included in the housing 80, the members are disposed about one another to provide the housing with a variety of flexibility, hardness, and/or stiffness characteristics as desired. As such the housing 80 may be constructed of any of a wide variety of materials including metal(s), polymer(s), natural rubber, silicone, multilayer materials, urethanes, Pebax, HDPE, etc.

When the stent 70 is properly positioned on the balloon 16, such as in the manner depicted in FIGS. 1-3, a proximal portion 72 of the stent 70 is also disposed about at least a portion of the secondary guidewire housing 80. When the stent 70 is thusly positioned about the balloon 16 and the housing 80, in some embodiments a portion of the housing 80 and/or the secondary guidewire 86 may be configured to extend distally through a cell opening 76 of the stent 70.

In some embodiments, the secondary guidewire 86 is merely slid between the balloon 16 and the stent 70 without the use of a housing 80. In some embodiments, where the stent 70 is to be positioned substantially proximal to a side branch of a vessel bifurcation, the guidewire 86 and/or housing 80 may be configured to extend under the entire length of the stent 70.

In operation, the secondary guidewire 86 is initially advanced through the vessel 100 and into a side branch 102 of a bifurcation 104. By advancing the catheter assembly 10 along the secondary guidewire 86 in the manner described above, the balloon 16 and the stent 70 disposed thereabout will be rotated to align the secondary opening 78 of the stent 70 with the side branch vessel 102. Once properly positioned in this manner the collars 30 and 32 may be activated and the balloon 16 expanded to deliver the stent 70 such as in the manner depicted in FIG. 3. Once the stent 70 is delivered the balloon is deflated and the assembly is withdrawn from the vessel 100.

A therapeutic agent may be placed on the stent and/or other portion of the assembly 10 in the form of a coating. Often the coating includes at least one therapeutic agent and at least one polymer.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

In some embodiments, the balloon waists 20 and 22 may be reinforced or strengthened in any of a number of ways in order to provide an improved interface and seal between the collars 30 and 32 and the respective balloon waists 20 and 22 when in the activated state. In at least one embodiment the waists 20 and 22 may be constructed with or supplemented with one or more layers of a transition material or coating of one or more strands, fibers or layers of stainless steel or other suitable reinforcing material.

In some embodiments one or more hubs or other surface features may be provided adjacent to the balloon waists 20 and 22 in order to ensure that the balloon maintains its proper longitudinal position relative to the catheter shafts 12 and 14. In some cases however, the use of hubs may be considered to be undesirable as a hub may affect the flexibility of the portion of catheter adjacent thereto and provide an increase to the catheter's profile. To avoid such potential affects, in some embodiments the collars 30 and/or 32 may be provided with a shape which allows each collar to interfere with the longitudinal movement of the balloon 16 without affecting the rotational ability of the balloon 16 in the non-activated state. Some examples of collars 30 and 32 that are appropriately configured to prevent or limit the longitudinal movement of the balloon 16 relative to the shafts 12 and 14 are illustrated in FIGS. 5-10.

As is shown in FIGS. 5-10 the balloon 16 comprises a distal waist 20 and a proximal waist 22. Immediately and distally adjacent to the distal waist 20 is a distal cone 21 that extends at an angle radially outward from the distal waist when the balloon 16 is expanded. Immediately and proximately adjacent to the proximal waist 22 is a proximal cone 23 which extends at an angle radially outward from the proximal waist when the balloon is expanded. The balloon body portion 25 extends between the proximal and distal cones 21 and 23. The cones and body of the balloon 16 define a balloon interior 40 and a balloon exterior 41. The balloon interior 40 is in fluid communication with the inflation lumen 42.

Figure 5:
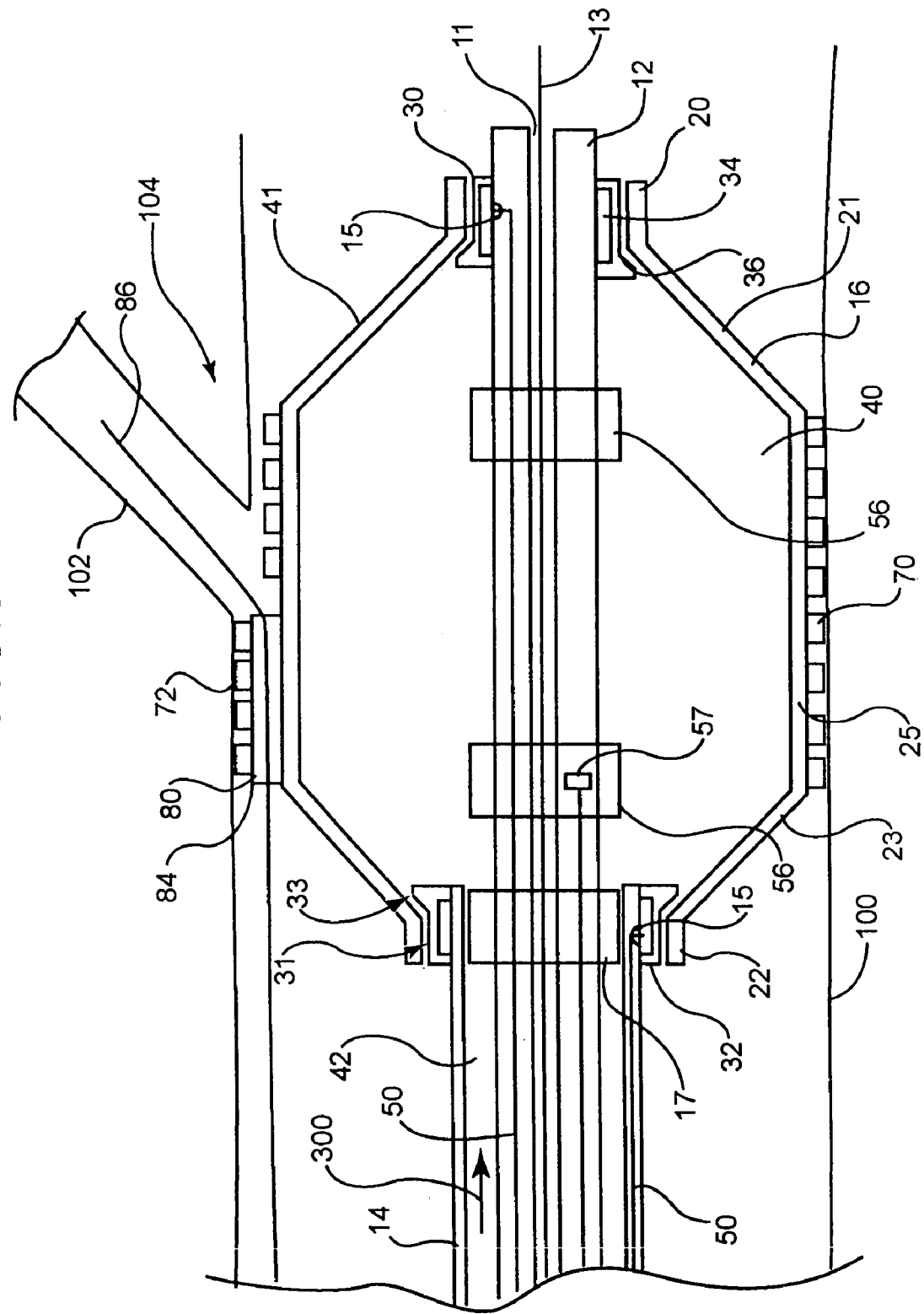
FIG. 5 is a longitudinal cross-sectional view of the embodiment shown in FIG. 2 wherein the catheter assembly is provided with an alternative collar configuration.
Figure 6:
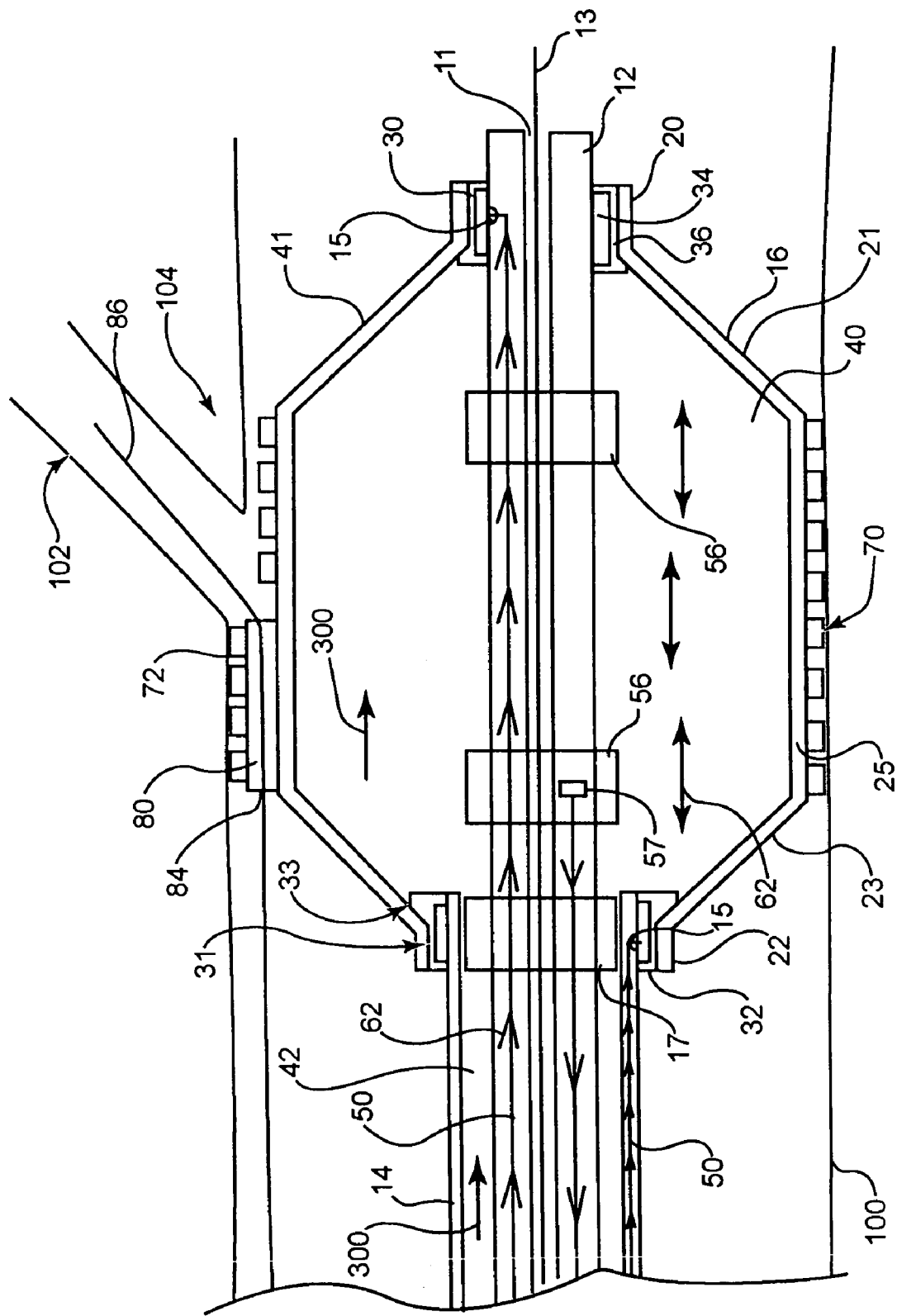
FIG. 6 is a longitudinal cross-sectional view of the embodiment shown in FIG. 5 shown during expansion of the balloon.

In the embodiment shown in FIGS. 5 and 6 each of the collars 30 and 32 may be characterized as having primary or body portion 31 and one or more lips or protrusions 33 which extend radially outward from the body portion 31. Each lip 33 is positioned within the balloon interior 40 and defines an angle relative to the body portion 31, which corresponds to the angle defined by the respective balloon waist and balloon cone adjacent thereto. The extension of each lip 33 into the balloon interior 40 acts to interfere with the respective balloon cone 21 or 23, thereby "trapping" the balloon 16 between the lips 33 of each collar 30 and 32.

In the non-activated state shown in FIG. 5 the lips 33 should be configured to engage a portion of the balloon 16 in order to minimize longitudinal movement of the balloon 16 relative thereto. In the activated state, such as is shown in FIG. 6, the body 31 and/or lip 33 of each collar 30 and 32 will sealingly engage the respective balloon waist and/or cone, such as in the manner depicted.

The lips 33 may extend into the balloon interior 40 to any desired extent. In order to maintain a minimum of profile however, it may be desirable to extend the lips into the interior 40 only to an extent sufficient to abut the respective waist 20 and 22 and/or a portion of the cones 21 and 23.

In addition to preventing or limiting longitudinal movement of the balloon 16 the shape of the collars 30 and 32, and particularly the shape of the lips 33 relative to the respective balloon cones 21 and 23, may also aid in preventing bunching and/or tearing of a deflated balloon 16 during withdrawal of the catheter assembly 10 from the body.

Figure 7:
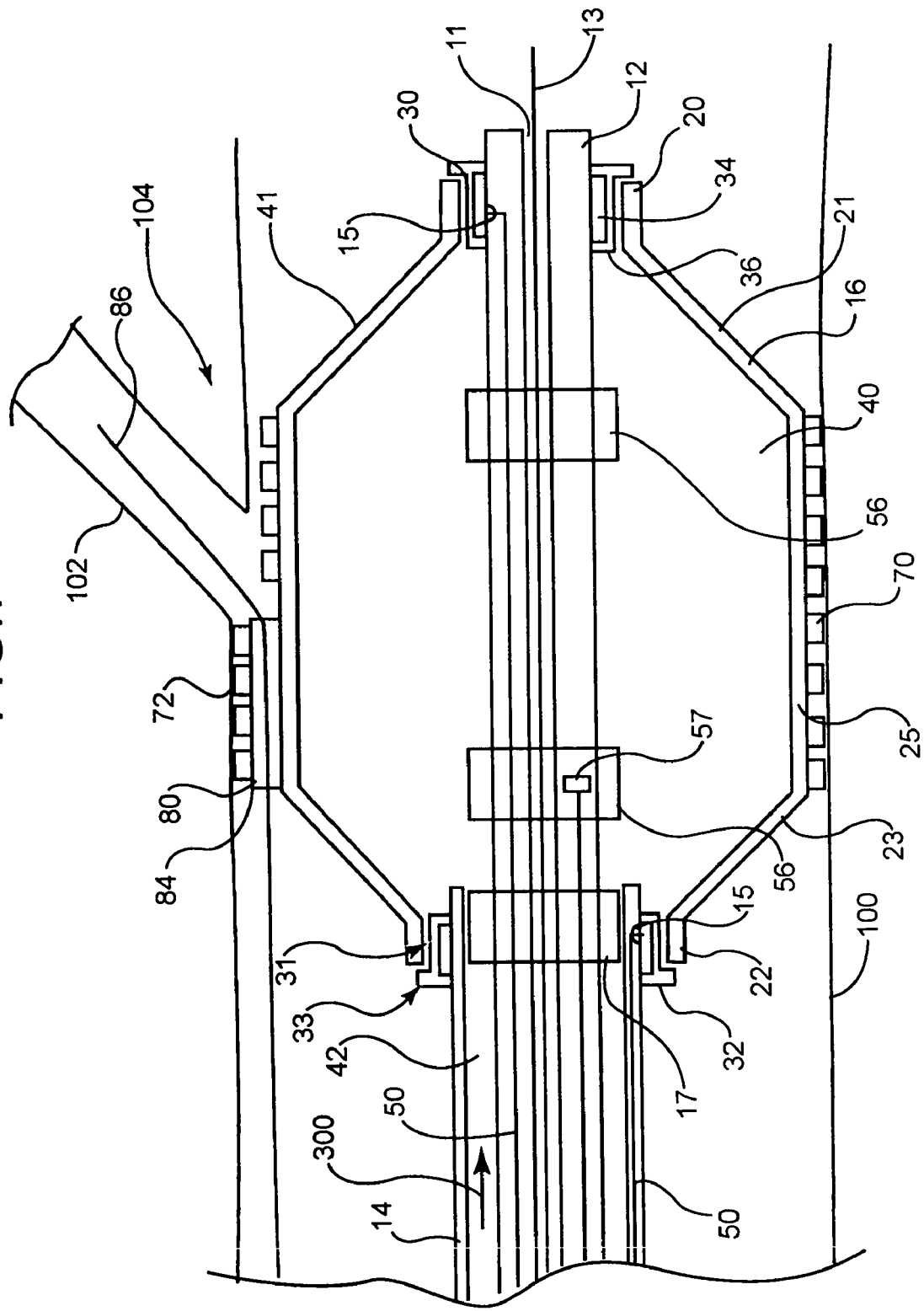
FIG. 7 is a longitudinal cross-sectional view of the embodiment shown in FIG. 2 wherein the catheter assembly is provided with an alternative collar configuration.
Figure 8:
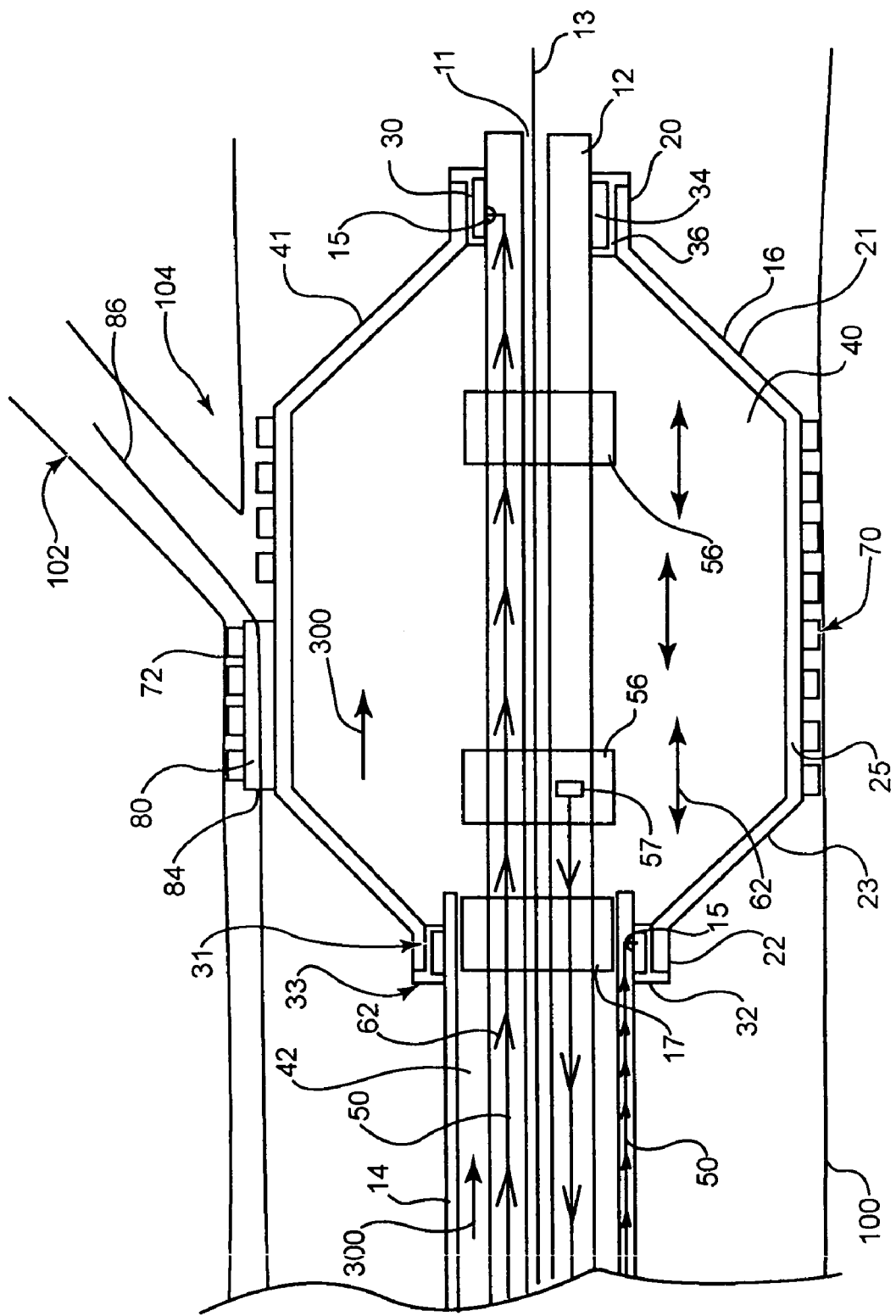
FIG. 8 is a longitudinal cross-sectional view of the embodiment shown in FIG. 7 shown during expansion of the balloon.

Collars 30 and 32 are not limited the arrangement of providing a lip 33 within the balloon interior 40. Collars 30 and 32 may be provided with numerous configurations and arrangements of a body portion 31 and one or more lips 33. In FIGS. 7 and 8 for example the lip 33 of each collar extends radially outward from the body portion 31 of each collar 30 and 32, but is positioned such that the lip is external to the balloon 16. While each lip 33 may have any length desired, each lip 33 preferably has a length which is sufficient to abut a respective waist 20 and 22 of the balloon in the non-activated state, such as is depicted in FIG. 7. When the collars are in the activated state, such as is shown in FIG. 8, the collars 30 and 32 sealingly engage at least two sides of the adjacent and respective waist 20 and 22 as shown.

Figure 9:
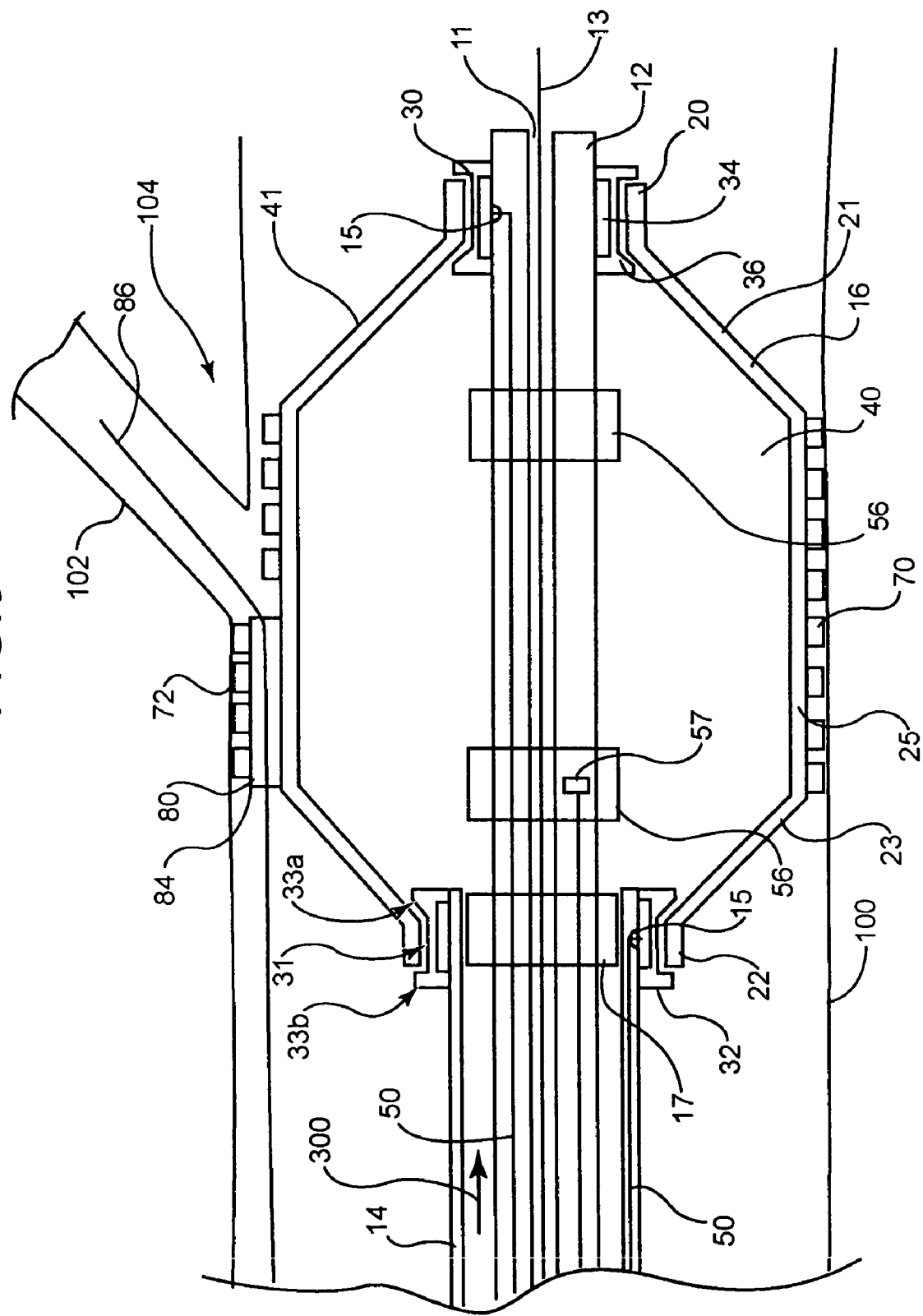
FIG. 9 is a longitudinal cross-sectional view of the embodiment shown in FIG. 2 wherein the catheter assembly is provided with an alternative collar configuration.
Figure 10:
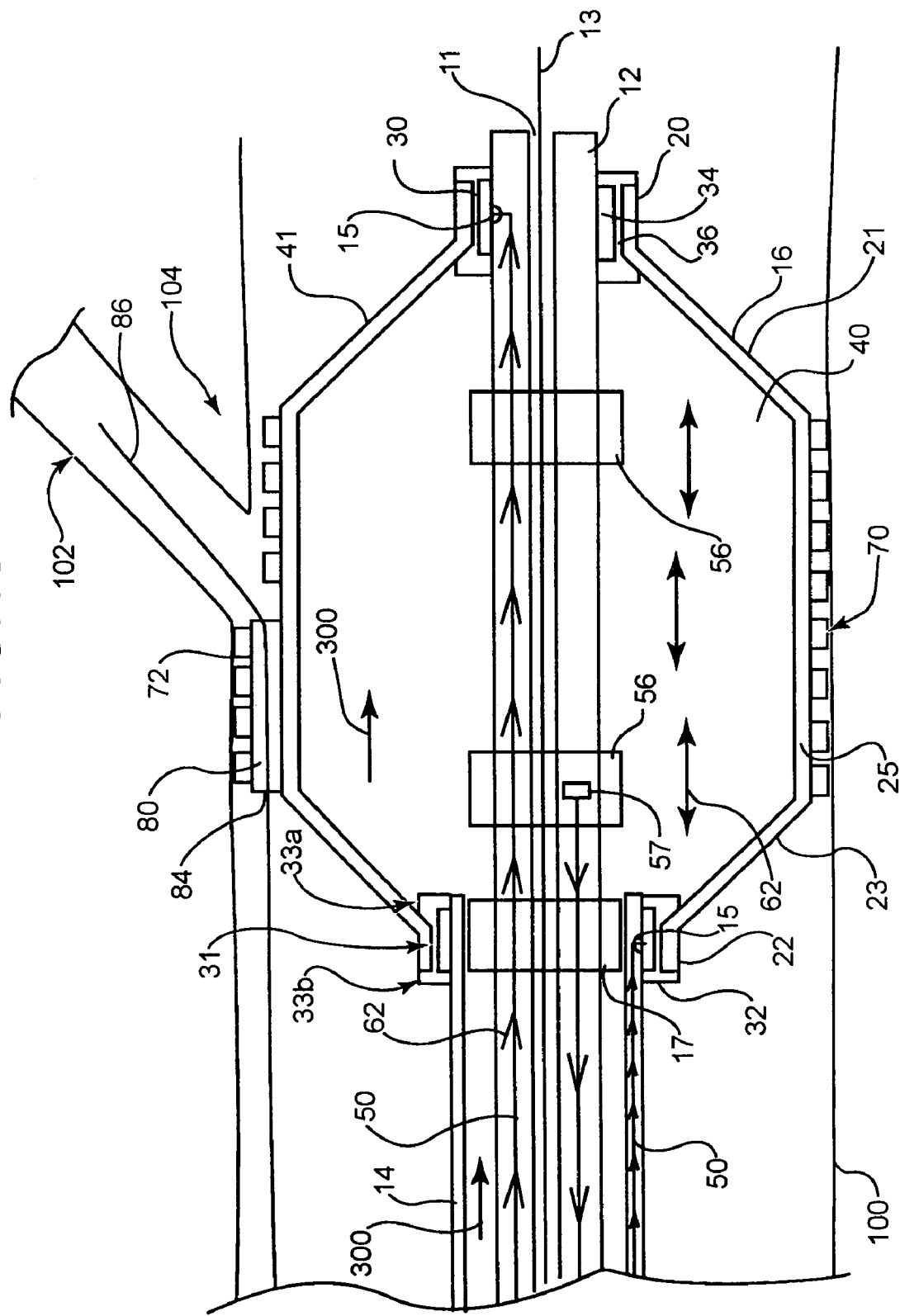
FIG. 10 is a longitudinal cross-sectional view of the embodiment shown in FIG. 9 shown during expansion of the balloon.

In yet another embodiment, an example of which is shown in FIGS. 9 and 10, each collar 30 and 32 is provided with a body portion 31 as well as two lips 33a and 33b. Lips 33a are positioned within the balloon interior 40, adjacent to a respective balloon cone 21 and 23, such as in the manner previously described in relation to FIGS. 5 and 6. Each lip 33b is positioned external and adjacent to a respective balloon waists 20 and 22, such as in the manner previously described in FIGS. 7 and 8. The resulting collar configuration ensures that longitudinal movement of the balloon 16 is limited to the distance provided between lips 33a and 33b. This distance may be adjusted to any extent desired merely by providing the collar body portion 31 with a longer or shorter length relative to the length of a balloon waist.

It is also noted that the above collar configurations are only examples of collar configurations which may be suitable for use with the catheter assembly 10. Other configurations may include the use of any of a variety of potential mechanical or other interfaces between the balloon and collars.

In some cases, the stent 70, or one or more portions of the assembly 10 thereof, may be configured to deliver one or more therapeutic agents to a delivery site within the vessel 100 or one or more areas adjacent thereto such as shown in FIGS. 2-3 and 45-10.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:

1. A catheter assembly comprising:
   an outer catheter shaft, the outer catheter shaft having a length and an outer surface;
   an inner catheter shaft, the inner catheter shaft having a length and an outer surface;
   a balloon, the balloon comprising a proximal balloon waist, a distal balloon waist and a body portion there between, a proximal balloon cone extending between the proximal balloon waist and the balloon body, a distal balloon cone extending between the distal balloon waist and the balloon body; the balloon having an expanded state and a unexpanded state, in the expanded state the body portion having an expanded diameter and in the unexpanded state the body portion having an unexpanded diameter that is less than the expanded diameter; and
   a proximal collar and a distal collar, the proximal collar fixedly engaged to the outer catheter shaft and the distal collar fixedly engaged to the inner catheter shaft, each collar having a body portion and at least one lip portion, the at least one lip portion extending radially outward from the body portion, each collar having a nonactivated state and an activated state, in the nonactivated state the balloon being rotatable around the proximal collar and the distal collar, in the nonactivated state each lip portion constructed and arranged to abut a portion of the balloon to prevent the balloon from moving longitudinally relative thereto, in the activated state the body portion of the proximal collar being expanded to sealingly engage at least a portion of the proximal balloon waist and the distal collar being expanded to sealingly engage at least a portion of the distal balloon waist.

2. The catheter assembly of claim 1 wherein the balloon defines a balloon interior, in the activated state a first lip portion of the proximal collar being engaged to at least a portion of the proximal balloon cone within the balloon interior and the a first lip portion of the distal collar being engaged to at least a portion of the distal balloon cone within the balloon interior.

3. The catheter assembly of claim 1 wherein the collars are actuated between the nonactivated state and the activated state by exposure to an electric current.

4. The catheter assembly of claim 3 further comprising at least one electrically conductive member, each collar being in electronic communication with the at least one electrically conductive member.

5. The catheter assembly of claim 4 further comprising a source of electrical current, the source being in electronic communication with the at least one electrically conductive member.

6. The catheter assembly of claim 4 wherein the at least one electrically conductive member is at least partially enclosed by the inner catheter shaft.

7. The catheter assembly of claim 6 wherein the at least one electrically conductive member is co-extruded with the at least one material of the inner catheter shaft.

8. The catheter assembly of claim 4 wherein the at least one electrically conductive member is at least partially enclosed by the outer catheter shaft.

9. The catheter assembly of claim 8 wherein the at least one electrically conductive member is co-extruded with the at least one material of the outer catheter shaft.

10. The catheter assembly of claim 4 wherein the outer catheter shaft is disposed about a portion of the inner catheter shaft and defines an inflation lumen therebetween which is in fluid communication with an interior of the balloon body.

11. The catheter assembly of claim 10 wherein the portion of the outer catheter shaft is disposed about a support ring, the inner catheter shaft extending through the support ring.

12. The catheter assembly of claim 4 wherein the proximal collar and the distal collar are comprised of electro-active material.

13. The catheter assembly of claim 12 wherein the electro-active material is an electro-active polymer (EAP), a carbon nano-tube structure (bucky paper) or any combination thereof.

14. The catheter assembly of claim 13 wherein the EAP material is selected from at least one member of the group consisting of: Poly-pyrrole (PPy), Poly-Aniline (PAni), Poly-Thiofene (PTH), Poly-Paraphenylene Vinylene (PPV), Nafion, and any combination thereof.

15. The catheter assembly of claim 12 wherein when the proximal collar and the distal collar are exposed to the electric current the electro-active material in each collar expands up to about 300 percent.

16. The catheter assembly of claim 13 wherein when the proximal collar and the distal collar are exposed to the electric current the EAP material in each collar expands about 0.5 percent to about 20 percent.

17. The catheter assembly of claim 12 wherein the proximal collar and the distal collar are further comprised of at least one electrically conductive marker, the electro-active material being a layer of material engaged to at least a portion of a surface of the at least one electrically conductive marker.

18. The catheter assembly of claim 17 wherein the at least one electrically conductive marker is constructed of at least one material of the group consisting of gold, platinum, silver, nitinol, and any combination thereof.

19. The catheter assembly of claim 18 wherein the at least one electrically conductive marker is in direct contact with a portion of the at least one electrically conductive member which radially extends through at least one opening in the catheter shaft.

20. The catheter assembly of claim 1 further comprising a secondary guidewire housing, the secondary guidewire housing comprising a substantially tubular member engaged to the balloon, the secondary guidewire housing defining a secondary guidewire lumen through which a secondary guidewire may be slidingly positioned.

21. The catheter assembly of claim 20 further comprising a balloon expandable stent, the stent being expandable from an unexpanded configuration to and expanded configuration, in the unexpanded configuration the stent being disposed about at least a portion of the balloon body.

22. The catheter assembly of claim 21 wherein at least a proximal portion of the stent overlays at least a portion of the secondary guidewire housing.

23. The catheter assembly of claim 21 wherein the stent comprises a plurality of interconnected members, wherein adjacent members define openings there between, one of the openings being a secondary opening through which the secondary guidewire radially extends.

24. The catheter assembly of claim 5 further comprising an inflation fluid, the inflation fluid being injected into the balloon in order to expand the balloon from the unexpanded state to the expanded state, the inflation fluid being electrically conductive.

25. The catheter assembly of claim 24 wherein the proximal collar, the distal collar, the at least one electrically conductive member, the inflation fluid and the source of electric current forming an electric circuit through which the electric current flows to place the collars in the activated state.

26. A catheter assembly comprising:
a catheter shaft, the catheter shaft having a length and an outer surface;
a balloon including a proximal balloon waist, a distal balloon waist, and a body portion therebetween, the body portion of the balloon having an expanded state and an unexpanded state, wherein the body portion has a first diameter in the expanded state and a second diameter in the unexpanded state, the second diameter less than the first diameter; and
one or more collars disposed radially between the outer surface of the catheter shaft and at least one of the proximal balloon waist and the distal balloon waist of the balloon, the one or more collars having a body portion and at least one lip portion, the at least one lip portion extending radially outward from the body portion, in the nonactivated state the at least one lip portion constructed and arranged to abut a portion of the at least one of the proximal balloon waist and the distal balloon waist of the balloon to prevent the balloon from moving longitudinally relative to the catheter shaft, the one or more collars including an electroactive polymer material having a contracted state and an expanded state, wherein the balloon is rotatable relative to the catheter shaft when the electroactive polymer material of the one or more collars is in the contracted state and the balloon is sealingly engaged to the catheter shaft when the electroactive polymer material of the one or more collars is in the expanded state.

27. The catheter assembly of claim 26, wherein the electroactive polymer material of the one or more collars is electrically actuatable between the contracted state and the expanded state.

28. The catheter assembly of claim 26, wherein the one or more collars are fixed to at least one of the proximal waist and the distal waist of the balloon.

29. The catheter assembly of claim 26, wherein the one or more collars are fixed to the catheter shaft.

30. A catheter assembly comprising:
a catheter shaft including a proximal end, a distal end, and a lumen extending at least partially therebetween;
a balloon disposed about at least a portion of the catheter shaft adjacent to the distal end, wherein the balloon includes a proximal waist and a distal waist; and
one or more electroactive polymers disposed radially between the catheter shaft and at least one of the proximal waist and the distal waist of the balloon, wherein the one or more electroactive polymers are fixed to the catheter shaft and configured to expand when activated by an electrical current, the one or more electroactive polymers having at least one lip portion extending radially outward to abut a portion of the proximal waist and/or the distal waist of the balloon to prevent the balloon from moving longitudinally relative to the catheter shaft;
wherein the balloon is rotatable relative to the catheter shaft when the one or more electroactive polymers are nonactivated and the balloon is sealingly engaged to the catheter shaft when the one or more electroactive polymers are activated.

* * * * *